US00PP24160P2

(12) United States Plant Patent
Kristiansen

(10) Patent No.: US PP24,160 P2
(45) Date of Patent: Jan. 14, 2014

(54) ***ASTER* PLANT NAMED 'VICTORIA XENIAN'**

(50) Latin Name: *Aster novi-belgii*
Varietal Denomination: Victoria Xenian

(75) Inventor: Kell Kristiansen, Sorø (DK)

(73) Assignee: Aster Klubben, Kerteminde (DK)

( * ) Notice: Subject to any disclaimer, the term of this patent is extended or adjusted under 35 U.S.C. 154(b) by 73 days.

(21) Appl. No.: 13/385,755

(22) Filed: Mar. 5, 2012

(51) Int. Cl.
*A01H 5/00* (2006.01)

(52) U.S. Cl.
USPC ..... Plt./355

(58) Field of Classification Search
USPC ..... Plt./355
See application file for complete search history.

*Primary Examiner* — Annette Para
(74) *Attorney, Agent, or Firm* — C. A. Whealy

(57) ABSTRACT

A new and distinct cultivar of *Aster* plant named 'Victoria Xenian', characterized by its compact, uniform, upright and mounded plant habit; freely branching growth habit; uniform and freely flowering habit; and decorative-type inflorescences with light red purple-colored ray florets.

2 Drawing Sheets

Botanical designation: *Aster novi-belgii*.
Cultivar denomination: 'VICTORIA XENIAN'.

BACKGROUND OF THE INVENTION

The present invention relates to a new and distinct cultivar of *Aster* plant, botanically known as *Aster novi-belgii* and hereinafter referred to by the name 'Victoria Xenian'.

The objective of the breeding program is to create new compact and fast-growing *Aster* plants with uniform and rounded plant growth habit, freely branching habit and attractive floret colors.

The new *Aster* originated from an open-pollination in March, 2008 in Aarslev, Denmark of *Aster novi-belgii* 'Victoria Mathilde', disclosed in U.S. Plant Pat. No. 19,930, as the female, or seed, parent with an unknown *Aster novi-belgii* seedling selection, as the male, or pollen, parent. The new *Aster* plant was discovered and selected by the Inventor as a single flowering plant within the progeny of the stated open-pollination in a controlled environment in Aarslev, Denmark in April, 2009.

Asexual reproduction of the new *Aster* plant by vegetative tip cuttings was first conducted in Aarslev, Denmark in September, 2009. Asexual reproduction by cuttings has shown that the unique features of this new *Aster* plant are stable and reproduced true to type in successive generations.

SUMMARY OF THE INVENTION

Plants of the new *Aster* have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Victoria Xenian'. These characteristics in combination distinguish 'Victoria Xenian' as a new and distinct *Aster* plant:

1. Compact, uniform, upright and mounded plant habit.
2. Freely branching growth habit.
3. Uniform and freely flowering habit.

4. Decorative-type inflorescences with light red purple-colored ray florets.

Plants of the new *Aster* differ from plants of the female parent, 'Victoria Mathilde', in the following characteristics:

1. Leaves of plants of the new *Aster* are broader than leaves of plants of 'Victoria Mathilde'.
2. Plants of the new *Aster* flower about eight to ten days earlier than plants of 'Victoria Mathilde'.
3. Plants of the new *Aster* have larger inflorescences than plants of 'Victoria Mathilde'.
4. Ray florets of plants of the new *Aster* flower are lighter in color than ray florets of plants of 'Victoria Mathilde'.

Plants of the new *Aster* can be compared to plants of *Aster novi-belgii* 'Victoria Pink Fanny', not patented. In side-by-side comparisons conducted in Aarslev, Denmark, plants of the new *Aster* differed from plants of 'Victoria Pink Fanny' in the following characteristics:

1. Plants of the new *Aster* were more upright than plants of 'Victoria Pink Fanny'.
2. Leaves of plants of the new *Aster* were broader than leaves of plants of 'Victoria Pink Fanny'.
3. Plants of the new *Aster* flowered about three to four days earlier than plants of 'Victoria Pink Fanny'.
4. Ray florets of plants of the new *Aster* were lighter in color than ray florets of plants of 'Victoria Pink Fanny'.

BRIEF DESCRIPTION OF THE PHOTOGRAPHS

The accompanying photographs illustrate the overall appearance of the new *Aster* plant showing the colors as true as it is reasonably possible to obtain in colored reproductions of this type. Colors in the photographs may differ slightly from the color values cited in the detailed botanical description which accurately describe the colors of the new *Aster* plant.

The photograph on the first sheet comprises a side perspective view of a typical flowering plant of 'Victoria Xenian' grown in a container.

The photograph on the second sheet comprises close-up views of the upper (top of the photograph) and lower surfaces (bottom of the photograph) of typical inflorescences and leaves of 'Victoria Xenian'.

DETAILED BOTANICAL DESCRIPTION

The aforementioned photographs and following observations and measurements describe plants grown during the late summer in 10.5-cm containers in a glass-covered greenhouse in Marslev, Denmark under environmental conditions and cultural practices which approximate those generally used in commercial container *Aster* production. During the production of the plants, day temperatures ranged from 19° C. to 20° C. and night temperatures ranged from 18° C. to 19° C. Plants were pinched one time and were twelve weeks old when the photographs and description were taken. In the following description, color references are made to The Royal Horticultural Society Colour Chart, 2007 Edition, except where general terms of ordinary dictionary significance are used.

Botanical classification: *Aster novi-belgii* 'Victoria Xenian'.

Parentage:

*Female, or seed, parent.*—*Aster novi-belgii* 'Victoria Mathilde', disclosed in U.S. Plant Pat. No. 19,930.

*Male, or pollen, parent.*—Unknown *Aster novi-belgii* seedling selection, not patented.

Propagation:

*Type.*—Terminal vegetative cuttings.

*Time to initiate roots, summer.*—About eight to ten days at temperatures of about 20° C.

*Time to initiate roots, winter.*—About ten days at temperatures of about 20° C.

*Time to produce a rooted young plant, summer.*—About twelve days at temperatures of about 20° C.

*Time to produce a rooted young plant, winter.*—About two weeks at temperatures of about 20° C.

*Root description.*—Medium in thickness, fibrous; white in color.

*Rooting habit.*—Moderately freely branching; medium density.

Plant description:

*Appearance.*—Herbaceous decorative-type potted *Aster*; compact and upright with lateral branches somewhat outwardly spreading; narrow inverted triangle with mounded crown; strong and freely branching growth habit with about seven primary lateral branches each with numerous secondary branches; low vigor to moderately vigorous growth habit.

*Plant height.*—About 21.1 cm.

*Plant width.*—About 12.6 cm.

*Lateral branches.*—Length: About 10.8 cm. Diameter: About 2 mm. Internode length: About 1.1 cm. Angle: Lateral stems are positioned about 25° from the main stem. Strength: Strong. Texture: Pubescent. Color: Close to 137B.

Foliage description:

*Arrangement.*—Alternate, simple; sessile.

*Length.*—About 4.1 cm.

*Width.*—About 9 mm.

*Shape.*—Narrowly oblong to narrowly oblanceolate.

*Apex.*—Acute to narrowly acute.

*Base.*—Cordate, decurrent.

*Margin.*—Entire, occasionally with one or two small teeth along the margins.

*Texture, upper and lower surfaces.*—Smooth, glabrous; leathery.

*Color.*—Developing leaves, upper surface: Close to 137B to 137C. Developing leaves, lower surface: Between 137D and 138B. Fully expanded leaves, upper surface: Close to 137B; venation, close to 146A. Fully expanded leaves, lower surface: Close to 147B; venation, 146A to 146B.

Inflorescence description:

*Appearance.*—Decorative-type inflorescence form with narrowly oblanceolate-shaped ray florets; inflorescences borne on terminal and axillary branches above and beyond the foliar plane; ray and disc florets arranged acropetally on a capitulum.

*Fragrance.*—None detected.

*Flowering response.*—Under natural conditions, plants flower during from mid-summer into the autumn in Denmark; response time, about six weeks.

*Inflorescence longevity.*—Inflorescences maintain good substance for about two weeks on the plant; inflorescences persistent.

*Quantity of inflorescences.*—Freely flowering habit with about 28 inflorescences developing per plant.

*Inflorescence buds.*—Height: About 1.3 cm. Diameter: About 1.5 cm. Shape: Broadly ovate to globular. Color: Close to 137B; towards the apex, close to 70A to 70B.

*Inflorescence size.*—Diameter: About 3.7 cm. Depth (height): About 2.1 cm. Diameter of disc: Disc florets have not been observed on plants of the new *Aster*. Receptacle height: About 3 mm. Receptacle diameter: About 3 mm. Receptacle color: Close to 144D.

*Ray florets.*—Length: About 1.7 cm. Width: About 3 mm. Shape: Narrowly oblanceolate. Apex: Obtuse. Base: Cuneate. Margin: Entire. Texture, upper and lower surfaces: Smooth, glabrous; slightly longitudinally ribbed. Orientation: Initially upright, then about 45° from vertical to perpendicular to peduncle. Number of ray florets per inflorescence: About 150 arranged in numerous whorls. Color: When opening, upper surface: Close to 77B. When opening, lower surface: Close to 77C to 77D. Fully opened, upper surface: Close to 77C; towards the base, close to N74C; color becoming closer to 77C with development. Fully opened, lower surface: Close to 77D; color becoming closer to 76C with development.

*Phyllaries.*—Number of phyllaries per inflorescence: About 80 arranged in about four whorls. Length: About 7 mm. Width: About 2 mm. Shape: Oblanceolate. Apex: Narrowly acute. Base: Cuneate. Margin: Entire. Texture, upper and lower surfaces: Smooth, glabrous. Color, upper and lower surfaces: Close to N137D.

*Peduncles.*—Length: About 2.2 cm to 2.5 cm. Diameter: About 1.5 mm. Angle: Upright to about 20° from vertical. Strength: Strong, flexible. Texture: Smooth, glabrous. Color: Close to 137C.

*Reproductive organs.*—Androecium: Not observed on plants of the new *Aster*. Gynoecium: Pistil length: About 2 mm. Stigma shape: Bi-parted. Stigma color: Close to 150D. Style length: About 1 mm. Style color: Close to 157A to 157D. Ovary color: Close to 145D.

*Seeds and fruits.*—Seed and fruit production has not been observed on plants of the new *Aster*.

Disease & pest resistance: Plants of the new *Aster* have not been observed to be resistant to pathogens and pests common to *Aster* plants.

Garden performance: Plants of the new *Aster* have been observed to be tolerant to rain, wind and high temperatures of about 35° C., and to be hardy to USDA Hardiness Zone 8.

It is claimed:

1. A new and distinct *Aster* plant named 'Victoria Xenian' as illustrated and described.

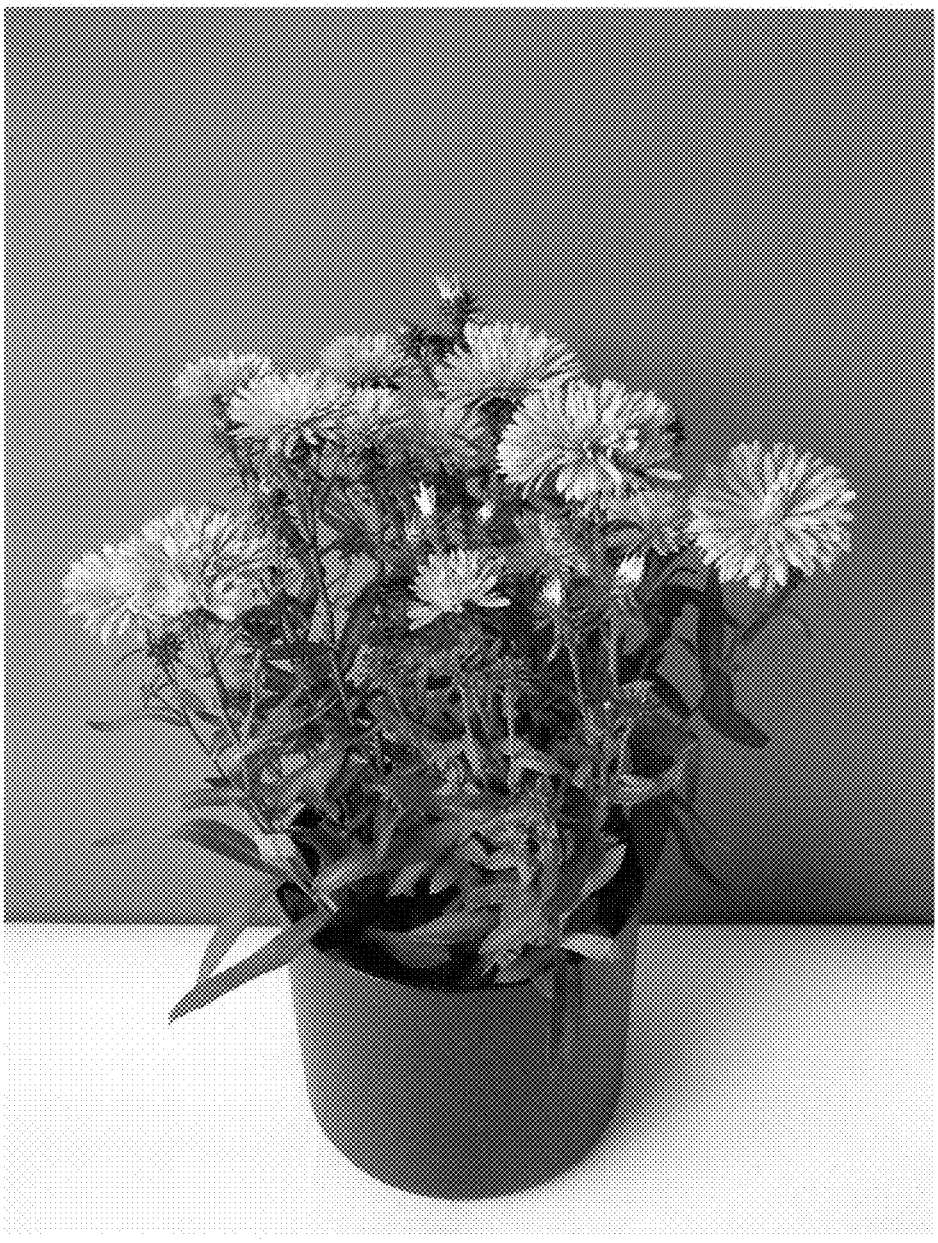

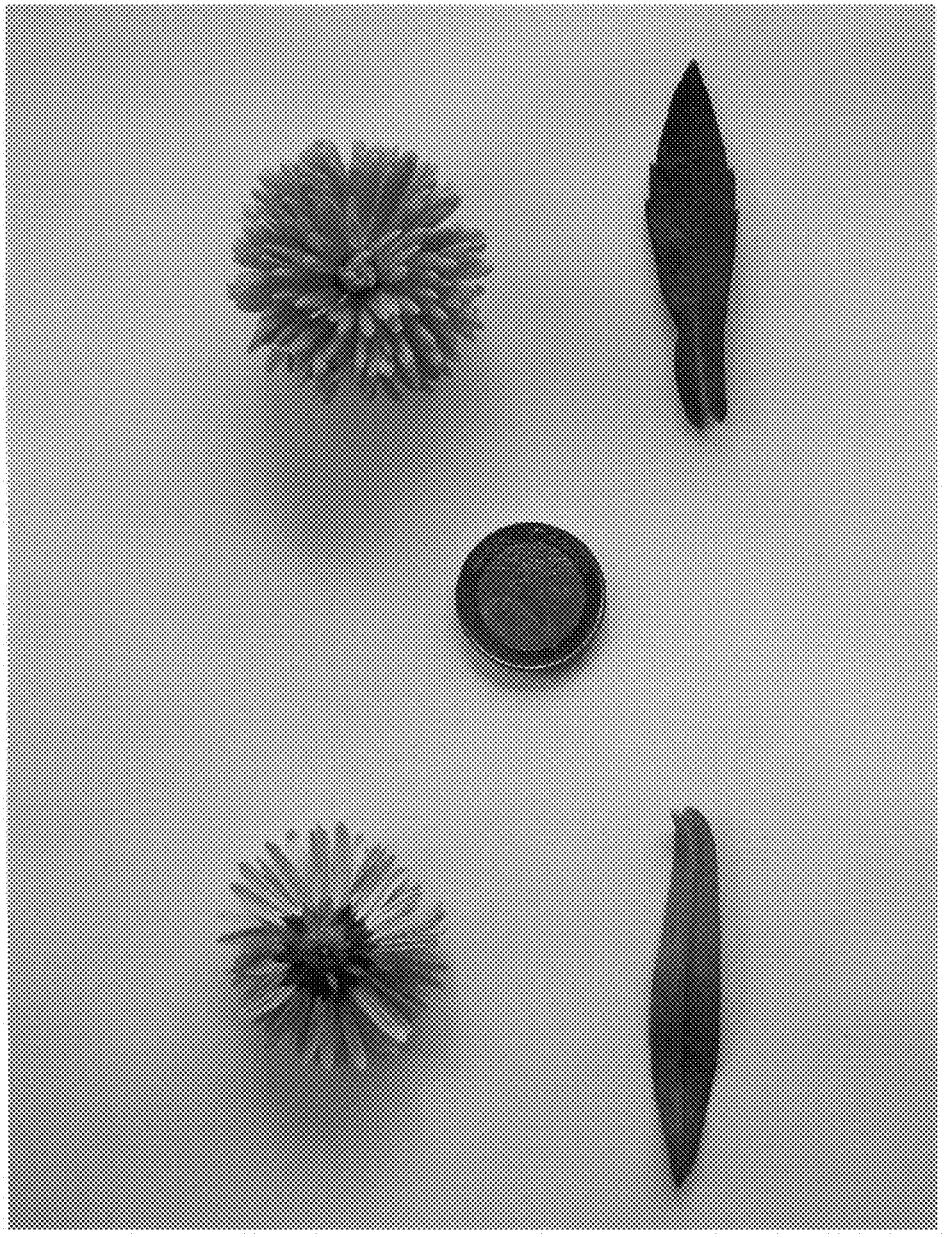

* * * * *